United States Patent [19]

Shaw et al.

[11] 4,301,030
[45] Nov. 17, 1981

[54] BI-CONTAINING METHACROLEIN OXIDATION CATALYSTS

[75] Inventors: Wilfrid G. Shaw, Lyndhurst; James E. Rinz, Bedford; Christos Paparizos, Willowick, all of Ohio

[73] Assignee: The Standard Oil Company, Cleveland, Ohio

[21] Appl. No.: 175,235

[22] Filed: Aug. 5, 1980

[51] Int. Cl.$^3$ .............................................. B01J 27/14
[52] U.S. Cl. ..................................... 252/435; 252/437
[58] Field of Search ................................ 252/435, 437

[56] References Cited

U.S. PATENT DOCUMENTS

| | | | |
|---|---|---|---|
| 3,976,688 | 8/1976 | Okiyama et al. | 252/437 |
| 4,017,423 | 4/1977 | White et al. | 252/437 |
| 4,042,533 | 8/1979 | Shaw et al. | 252/437 |
| 4,101,448 | 7/1978 | Shaw et al. | 252/437 |
| 4,166,190 | 8/1979 | White et al. | 252/437 X |
| 4,174,459 | 11/1979 | Sakamoto et al. | 252/435 X |
| 4,225,466 | 9/1980 | Wada et al. | 252/435 |

FOREIGN PATENT DOCUMENTS 1482686  8/1977  United Kingdom .

Primary Examiner—Delbert E. Gantz
Assistant Examiner—William G. Wright
Attorney, Agent, or Firm—Salvatore P. Pace; Herbert D. Knudsen; Larry W. Evans

[57] ABSTRACT

Compositions of the empirical formula:

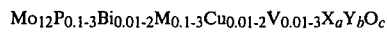

$$Mo_{12}P_{0.1-3}Bi_{0.01-2}M_{0.1-3}Cu_{0.01-2}V_{0.01-3}X_aY_bO_c$$

where
M is at least one of K, Rb and Cs;
X is at least one of Ba, Zn, Ga, Cd and Ti when $a>0$;
Y is at least one of Ca, Mg, Ta, Zr, Ce, Ni, Co, Cr, Fe and Tl when $b>0$;
a is a number of 0 to about 2;
b is a number of 0 to about 2; and
c is a number that satisfies the valence requirements of the other elements present, are excellent catalysts for the oxidation of methcrolein to methacrylic acid.

10 Claims, No Drawings

BI-CONTAINING METHACROLEIN OXIDATION CATALYSTS

BACKGROUND OF THE INVENTION

1. Field of the Invention

This invention relates to catalysis. In one aspect, the invention relates to novel catalytic compositions of phosphorus, molybdenum, bismuth, copper, vanadium and an alkali metal while in another aspect, the invention relates to a process employing these catalysts for the oxidation of methacrolein to methacrylic acid.

2. Description of the Prior Art

The art is replete with various phosphomolybdic acid catalysts useful for the oxidation of acrolein to acrylic acid. See for example U.S. Pat. Nos. 4,101,448, 4,115,441, 4,042,533 and 4,166,190. However, not only do many of these catalysts contain tungsten but most are not suitable, at least from a commercial perspective, for the oxidation of methacrolein to methacrylic acid. Of those catalysts that are suitable from a commercial perspective, none are entirely so. All are subject to improvement in methacrylic acid selectively and thermal stability. Examples of catalysts now taught to be suitable for methacrolein oxidation are those of Belgium Pat. No. 823,897, Great Britian Pat. No. 1,482,686, U.S. Pat. No. 3,976,688 and U.S. Pat. No. 4,017,423. The Belgium patent teaches a phosphomolybdic acid catalyst that can be combined with any number of optional components; the British patent teaches a P—Mo—Cu—V—W catalyst that also can be combined with optional components; U.S. Pat. No. 3,976,688 teaches a catalyst similar to the phosphomolybdic acid catalyst of the Belgium patent but containing Rb, Cs or K; and U.S. Pat. No. 4,017,423 teaches a promoted Rb—Mo—P catalyst.

SUMMARY OF THE INVENTION

According to this invention, compositions of the empirical formula:

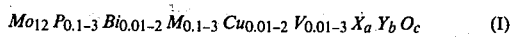

$$Mo_{12} P_{0.1-3} Bi_{0.01-2} M_{0.1-3} Cu_{0.01-2} V_{0.01-3} X_a Y_b O_c \quad (I)$$

where
M is at least one of K, Rb and Cs;
X is at least one of Ba, Zn, Ga, Cd and Ti when $a>0$;
Y is at least one of Ca, Mg, Ta, Zr, Ce, Ni, Co, Cr, Fe and Tl when $b>0$;
a is a number of 0 to about 2;
b is a number of 0 to about 2; and
c is a number that satisfies the valence requirements of the other elements present,
are excellent catalysts for the oxidation of methcrolein to methacrylic acid. These catalysts demonstrate both excellent selectivity for methacrylic acid and excellent thermal stability.

DETAILED DESCRIPTION OF THE INVENTION

Catalyst:

As is evident from formula I, the catalytic composition of this invention is at least a seven element material, i.e., a material containing molybdenum, phosphorus, bismuth, alkali metal (M), copper, vanadium and oxygen all in designated, proportional amounts. Preferably, the subscript value of phosphorus in formula I is about 0.8 to 1.5, of bismuth about 0.15 to 1, of alkali metal (M) about 0.15 to 2, of copper about 0.2 to 0.8 and of vanadium about 0.2 to 0.8.

Preferred catalysts of this invention are those where a is greater than 0 ($a>0$), and preferably a number of about 0.01–2. These preferred catalysts demonstrate unusually good methacrylic acid selectivities, particularly those where X is zinc, cadmium, titanium or barium. These preferred catalysts can be further enhanced, at least in terms of activity and, in some cases, thermal stability, by the addition of yet another component, here designated Y. When component Y is present ($b>0$), it is generally as calcium, magnesium, thallium, tantalum or zirconium.

As is taught by formula I, certain of the components can be combinations of two or more elements, e.g., X can be a combination of barium and zinc. In such instances, the subscript value represents the sum of the elements (e.g. for X, the sum of barium and zinc is equal to a which is less than or equal to about 2). Generally M, X, and Y each represent but a single element.

Particularly preferred catalytic compositions are eight element or component (including oxygen) catalysts where M is rubidium or potassium, X is zinc or cadmium, a is about 0.05 to about 0.5 and b is 0.

The exact structure or element arrangement of these catalysts are not known but the metal and phosphorus components are present in the form of their oxides, acids or oxide or oxyacid complexes. However, the compositions of formula I are known not to be a mere physical mixture of their components but rather unique heteropolyacids where the individual components are chemically and/or physically bonded to one another.

The catalytic compositions of this invention can be used either in the 100% active form or in a diluted form, i.e. supported or unsupported. Suitable support materials include silica, titania, alumina, zirconia, silicon carbide, boron, various phosphates, etc., with low surface area (about 1 m$^2$/g) alumina a preferred support material. If a support is used, the catalytic composition is generally present in an amount of at least about 20 weight percent, based on the combined weight of the support and the catalytic composition, and preferably in an amount of at least about 30 weight percent.

The catalytic compositions of this invention can be prepared in any one of a number of different methods, the particular method employed being a matter of convenience. Typically, the catalysts are prepared by mixing the appropriate catalyst ingredients in the proper proportions in an aqueous mixture, drying the resulting aqueous slurry with or without a reducing agent, and calcining the product. The ingredients can be added in any order during the preparation procedure but certain orders are preferred, particularly the mixing of the metallic ingredients prior to the addition of phosphorus (generally in the form of phosphoric acid). The ingredients employed can be the oxides, halides, nitrates, acetates or other salts of the particular metals or elements added, and particularly preferred is the use of water soluble salts of the metal components. If a support is used, the material comprising the support may be incorporated into the catalyst along with the other ingredients or the catalyst composition may be coated and/or impregnated onto or into a core. After the catalyst ingredients have been combined to form an aqueous slurry, the slurry is taken to dryness and the dried solid obtained is heated in the presence of air, nitrogen, nitric oxide or a mixture of any two or more of these gases at temperatures between about 300° and 420° C. This calcination can take place outside the catalytic reactor or an in situ activation can be utilized. Other methods of preparation are broadly taught in the art.

Oxidation of Methacrolein:

In another embodiment of this invention, the compositions of formula I are highly effective catalysts for the oxidation of methacrolein to methacrylic acid. These catalytic compositions are used in the same manner as known catalytic compositions. This is a known reaction involving generally the contact of methacrolein with molecular oxygen at an elevated temperature in the presence of a catalytic amount of catalyst. This particular embodiment of the invention is the use of these novel catalytic compositions within the parameters of the known art process.

Exemplary of this known process is the contacting of gaseous methacrolein with molecular oxygen in the presence of steam at a temperature between about 275° and about 340° C. The ratio of the reactants can vary widely with mole ratios of molecular oxygen to aldehyde of about 1 to 5 being typical. The amount of steam can also vary widely from a small amount generated in the reaction to 20 or more moles of steam per mole of aldehyde. Preferably, about 1 to 10 moles of steam per mole of aldehyde is employed in the reactant feed. In certain embodiments of this invention, recycle gas (principally $N_2$, $O_2$, $CO_2$ and CO) can be used with or instead of steam. Molecular oxygen is most conveniently added as air.

The oxidation reaction may be conducted in a fixed-bed, fluid-bed or transfer line reactor using atmospheric, superatmospheric or subatmospheric pressure. The contact time of reactants over the catalyst can vary from a fraction of a second to twenty or more seconds, the exact time dependent upon other reaction conditions, such as catalyst composition, feed composition, temperature, pressure, reactor, etc.

Although the catalytic compositions of this invention find particular usefulness in the oxidation of methacrolein to methacrylic acid, they are also useful in other oxidation reactions. For example, these catalytic compositions are useful in the oxidation of acrolein to acrylic acid.

The following examples are illustrative of certain specific embodiments of this invention. Unless otherwise indicated, all parts and percentages are by weight.

SPECIFIC EMBODIMENTS

Catalyst Preparation:

The catalyst of the following examples were prepared by dissolving, with stirring, ammonium heptamolybdate in distilled water and heating the resulting solution to 30°–35° C. While continuously stirring the solution and maintaining its temperature, the alkali metal hydroxide was added followed by the halide or hydroxide of the X component. After 15 minutes, the copper acetate and ammonium metavanadate solutions were added followed by addition of a bismuth trichloride/hydrochloric acid solution. The resulting slurry was then heated to about 70° C. for 2 hours after which time the halide or hydroxide of Y was added. Phosphoric acid ($H_3PO_4$) was the last material added after which stirring and heating was continued for 30 minutes and the pH of the slurry was adjusted to 5.6. The mixture was then evaporated to a thick paste and the catalyst precursor dried in an oven at 110°–120° C. The powder was then coated onto ⅛ in. Alundum spheres (alumina supports) so that the powder coating (i.e. the catalyst) constituted about 35 weight percent of the coated spheres.

As to those catalysts not having an X and/or Y component, they were prepared by essentially the same procedure except the steps adding the X and/or Y component(s) were eliminated.

Process Procedure and Conditions:

The reactions were conducted in a 20 cc, downward flow, fixed-bed reactor. All examples were performed in the same manner: first, one hour at 370° C. with air flow (no feed) and second, one hour at 345° C. with feed before the temperature was dropped to the reaction temperature. After a short stabilization period, a 15 min. run was conducted to obtain sufficient reactor effluent. The off-gas rate was measured with a soap-film meter and an off-gas composition was determined at the end of the run with the aid of a Perkin-Elmer 154 gas chromatograph. At the end of the recovery run, the entire scrubber liquid was diluted with distilled water to about 100 grams. A weighed amount of methanol was used as an internal standard in a 20 aliquot of the dilute solution. A one microliter sample was then analyzed in a Varian Model 3700 gas chromatograph fitted with a flame ionization detector and a Chromsorb 107 column 60/80 mesh. Total amounts of organic acids were determined by titrating 25 cc of the liquid with 0.1 N sodium hydroxide. The split between methacrylic, acrylic and acetic acid was determined from the gas chromatographic analysis.

The following process conditions were employed:
Pressure—atmospheric
Run Time—15 min.
Contact Time—3.2 sec.
Feed Ratio—methacrolein/water/air: 1/4/10.5
Temperature (°C.)—315
VVH[1]—35.

[1] Volume of methacrolein per volume of catalyst per hour.

The results of these experiments are reported in Table I.

TABLE I

| | | METHACROLEIN OXIDATION | | | | | | | | |
|---|---|---|---|---|---|---|---|---|---|---|
| Example | Catalyst Composition | Reactor Temp (°C.) | WWH[4] | MAA[1] | MA[2] (Unreac) | Acetic Acid | $CO_2$ | CO | MAA[3] | Carbon Balance |
| 1 | $Mo_{12} P_1 Rb_1 Bi_{.25} Cu_{.25} V_{.25} O_c$ | 305 | 0.100 | 69.2 | 13.8 | 4.7 | 5.5 | 4.9 | 80.3 | 96.5 |
| 2 | $Mo_{12} P_1 Rb_1 Bi_{.25} Cu_{.25} V_{.25} Ba_{.1} O_c$ | 310 | 0.105 | 70.5 | 15.8 | 4.0 | 5.2 | 3.9 | 83.0 | 98.2 |
| 3 | $Mo_{12} P_1 Rb_1 Bi_{.25} Cu_{.25} V_{.25} Ti_{.1} O_c$ | 300 | 0.106 | 69.5 | 16.2 | 3.8 | 5.6 | 3.8 | 83.0 | 96.2 |
| 4 | $Mo_{12} P_1 Rb_1 Bi_{.25} Cu_{.25} V_{.25} Zn_{.1} O_c$ | 315 | 0.100 | 67.8 | 20.0 | 3.3 | 4.5 | 3.3 | 84.7 | 101.2 |
| 5 | $Mo_{12} P_1 Rb_1 Bi_{.25}^1 Cu_{.25} V_{.25} Cd_{.1} O_c$ | 305 | 0.106 | 68.3 | 18.9 | 3.4 | 5.0 | 3.4 | 84.2 | 99.7 |
| 6 | $Mo_{12} P_1 Rb_1 Bi_{.25} Cu_{.25} V_{.25} Ga_{.1} O_c$ | 305 | 0.111 | 69.0 | 16.3 | 4.0 | 5.5 | 3.9 | 82.5 | 95.9 |

TABLE I-continued

| | | METHACROLEIN OXIDATION | | | | | | | | |
|---|---|---|---|---|---|---|---|---|---|---|
| Example | Catalyst Composition | Reactor Temp (°C.) | WWH[4] | MAA[1] | MA[2] (Unreac) | Acetic Acid | $CO_2$ | CO | MAA[3] | Carbon Balance |
| 7 | $Mo_{12}P_1Rb_1Bi_{.25}Cu_{.25}V_{.25}Ba_{.2}O_c$ | 301 | 0.114 | 72.0 | 11.5 | 4.2 | 6.7 | 4.5 | 81.3 | 101.3 |
| 8 | $Mo_{12}P_{1.33}Cs_1Bi_{0.25}Cu_{0.25}V_{0.5}Ba_{0.1}O_c$ | 304 | 0.105 | 74.3 | 12.1 | 3.9 | 5.4 | 3.4 | 84.5 | 100.5 |

[1]Methacrylic Acid Yield = Moles of Methacrylic Acid Recovered × 100/Moles of Methacrolein Fed
[2]Unreacted Methacrolein
[3]Methacrylic Acid Selectivity = Moles of methacrylic Acid Recovered × 100/Moles of Methacrolein Reacted
[4]WWH = Weight of Methacrolein/Weight of Catalyst/Hour The data of Table I shows the excellent yield of methacrylic acid and selectivity to methacrylic acid obtained by the use of the catalyst of this invention. Of particular note are those catalysts promoted with one or both of the X and Y components. The selectivity of these catalysts are superior to the catalyst not so promoted.

Although the invention has been described in considerable detail through the preceding examples, these examples are for the purpose of illustration only and it is understood that variations and modifications can be made by one skilled in the art without departing from the spirit and scope of the invention.

The claimed invention is:

1. A catalytic composition of the empirical formula:

$$Mo_{12}P_{0.1-3}Bi_{0.1-2}M_{0.1-3}Cu_{0.1-2}V_{0.1-3}X_aY_bO_c \quad (I)$$

wherein
M is at least one of K, Rb and Cs;
X is at least one of Ba, Zn, Ga, Cd and Ti;
Y is at least one of Ca, Mg, Ta, Zr, Ce, Ni, Co, Fe and Tl when b>0;
a is a number greater than 0;
b is a number of 0 to about 2; and
c is a number that satisfies the valence requirements of the other elements present.

2. The composition of claim 1 wherein M is potassium or rubidium.

3. The composition of claim 2 where X is barium, zinc, cadmium or titanium.

4. The composition of claim 3 where b is 0.

5. The composition of claim 3 where b>0.

6. The composition of claim 5 where Y is calcium, magnesium, thallium, tantalum or zirconium.

7. The composition of claim 4 where the subscript of phosphorus in formula I is a number of about 0.8 to about 1.6, of bismuth a number of about 0.15 to 1, of M a number of about 0.1 to 2, of copper a number of about 0.2 to 0.8 and of vanadium a number of about 0.2 to 0.8.

8. The composition of claim 7 in essentially 100% active form.

9. The composition of claim 7 diluted with a support.

10. The composition of claim 9 where the support is a low surface area alumina.

* * * * *